US00PP30125P3

(12) United States Plant Patent
Goffreda et al.

(10) Patent No.: US PP30,125 P3
(45) Date of Patent: Jan. 22, 2019

(54) NECTARINE TREE NAMED 'NJN102'

(50) Latin Name: ***Prunus persica* var. *nucipersica***
Varietal Denomination: NJN102

(71) Applicant: RUTGERS, THE STATE UNIVERSITY OF NEW JERSEY, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 67 days.

(21) Appl. No.: 15/530,542

(22) Filed: Jan. 26, 2017

(65) Prior Publication Data

US 2018/0213693 P1 Jul. 26, 2018

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./156, 180, 187, 190
See application file for complete search history.

(56) References Cited

PUBLICATIONS

Callahan Michigan Show Peach and Plum Great Lakes Expo, Plums, Pluots, Flat Peach, and Other Novel Stone Fruits Nov. 22, 2016, retrieved on May 1, 2018, retrieved from the Internet at www.glexpo.com/summaries/2016summaries/Peach-Plum.pdf, 13 pp. (Year: 2016).*

* cited by examiner

*Primary Examiner* — Susan McCormick Ewoldt
*Assistant Examiner* — Karen M Redden
(74) *Attorney, Agent, or Firm* — Patrick J. Daugherty; Daugherty & Del Zoppo Co., LPA

(57) ABSTRACT

A new and distinct nectarine variety of *Prunus persica* var. *nucipersica* named 'NJN102' is provided. This variety is distinguished from other nectarine varieties by its unique combination of showy flowers, fruit that ripen in early-midseason, glossy fruit with an attractive bright orange-red ground color, semi-freestone fruit with a juicy, melting texture and sweet, moderately acidic flavor, and excellent production of firm fruit that maintain their eating quality following cold storage.

6 Drawing Sheets

Latin name of genus and species of the plant claimed: *Prunus persica* var. *nucipersica.*

Variety denomination: 'NJN102'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of nectarine tree named 'NJN102'. Our new tree resulted from crossing 'Fantasia' (non-patented) nectarine as the seed parent with 'Eastern Glo' (U.S. Plant Pat. No. 7,890) nectarine tree, as the pollen parent. The new variety differs from seed parent 'Fantasia' in that the new variety ripens about four weeks earlier, and has been more tolerant to bacterial leaf spot in certain years. The new variety differs from pollen parent 'Eastern Glo' in that the new variety has been cold hardy to −20° C. and has good eating quality, while the pollen parent has had light crops after exposure to −20° C. and generally has fair eating quality. The resulting tree was selected when growing in a cultivated area as the $44^{th}$ tree in the $21^{st}$ row of Block H at a fruit research farm in Cream Ridge, N.J.

BRIEF SUMMARY OF THE INVENTION

The 'NJN102' differs from the related cultivar 'Crimson Gold' (U.S. Plant Pat. No. 2,825) in that 'NJN102' produces larger fruit, and the trees of 'NJN102' are more tolerant of bacterial leaf spot (Xanthomonas campestris pv. pruni) than 'Crimson Gold.' The 'NJN102' variety is also distinguished from other nectarine varieties due to the following unique combination of characteristics:

Nearly round fruit with a low tendency to split.

Glossy fruit with an attractive bright orange-red ground color.

Excellent production of firm fruit that ripen in early-mid-season.

Fruit with a good to very good eating quality.

The variety was asexually reproduced at a fruit research farm in Cream Ridge, N.J. Asexual reproduction of this new variety by budding onto 'Lovell' peach seedling rootstock (non-patented) shows that the foregoing characteristics are so reproduced.

The following detailed description concerns the original tree, 'NJN102'. The original tree and asexual progeny have been observed growing in a cultivated area at the fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966).

BRIEF DESCRIPTION OF THE DRAWINGS

This new variety is illustrated by the accompanying photographic drawings, depicting the nectarine tree at approximately six (6) years old by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
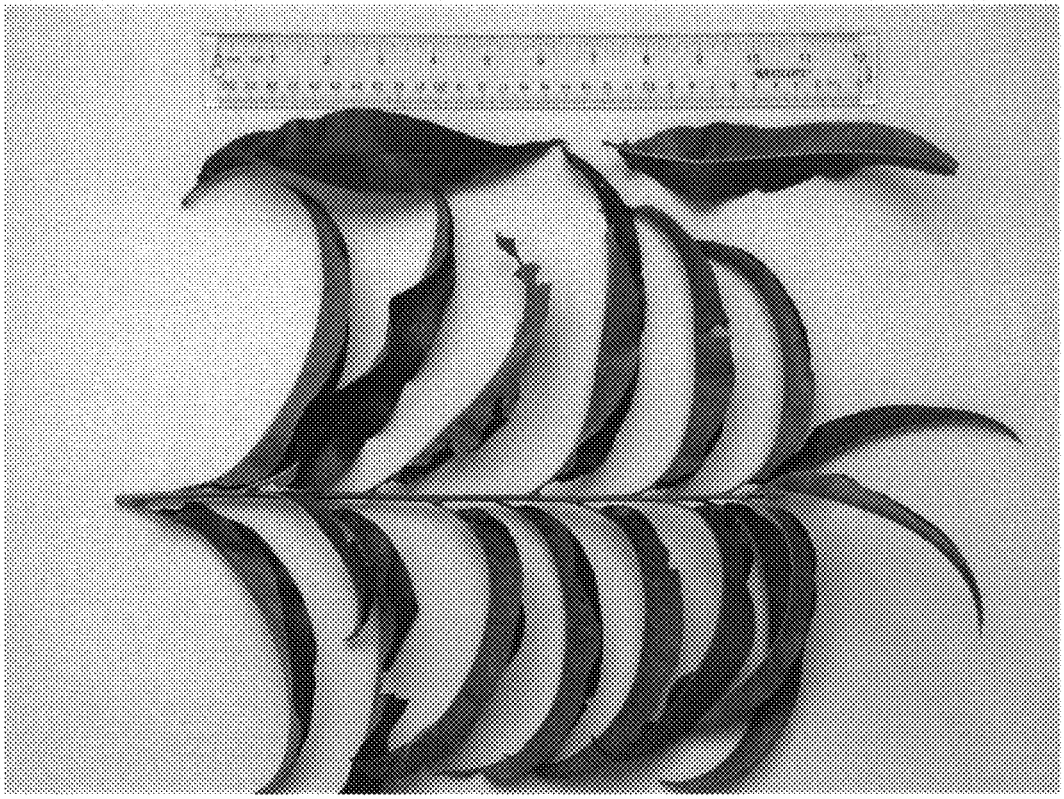
FIG. 1 is a color photograph taken on Aug. 16, 2013 of a characteristic twig of 'NJN102' in late spring bearing typical leaves of the foliage.
Figure 2:
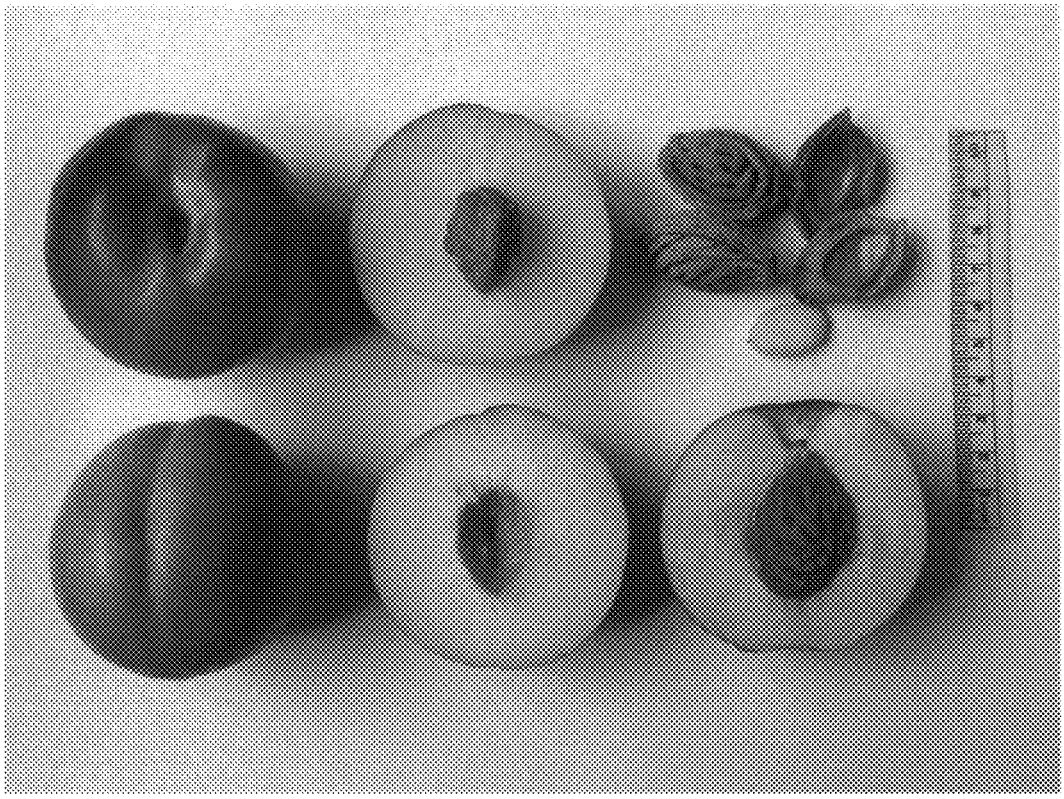
FIG. 2 is a color photograph taken on Aug. 8, 2013 of characteristic mature fruit and stones of 'NJN102'. Whole fruit are presented in three positions and both a transverse and longitudinal cross section to illustrate that the pericarp does not adhere to the pit when the fruit is mature. The stones exemplify the obovate shape and the chains of pits and grooves on the surface of the stone.
Figure 3:
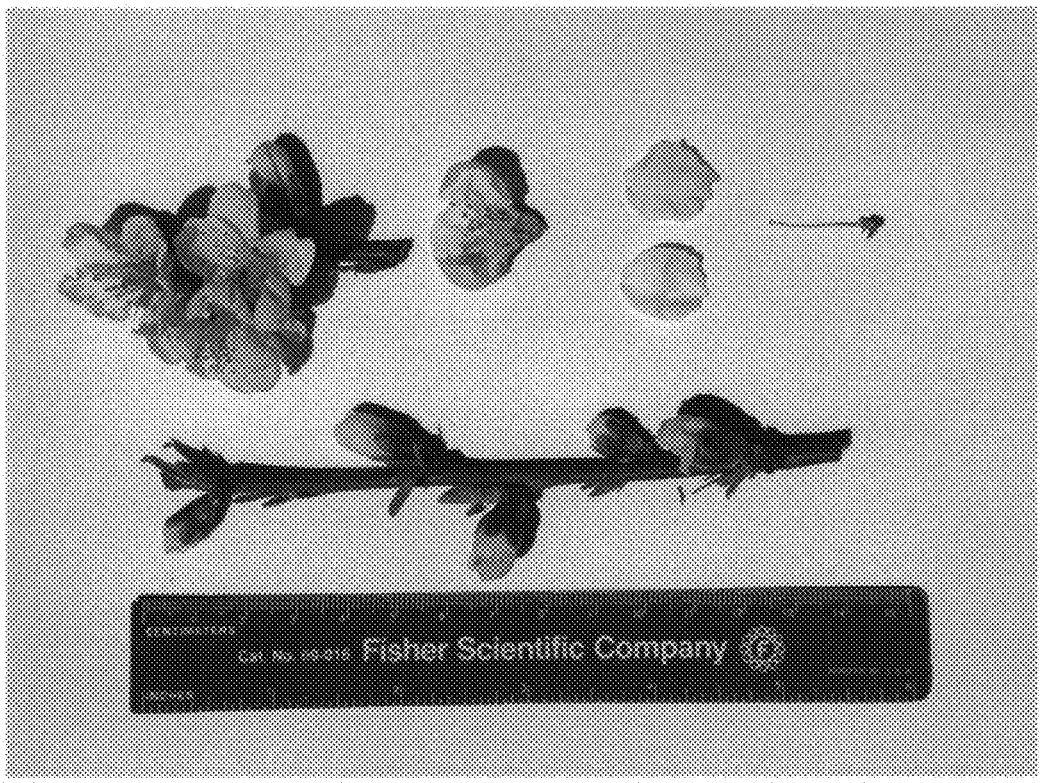
FIG. 3 is a color photograph of a characteristic twig that illustrates the typical flower buds and large, showy flowers of 'NJN102' observed on a tree at the fruit research in Cream Ridge, N.J. on Apr. 23, 2014.
Figure 4:
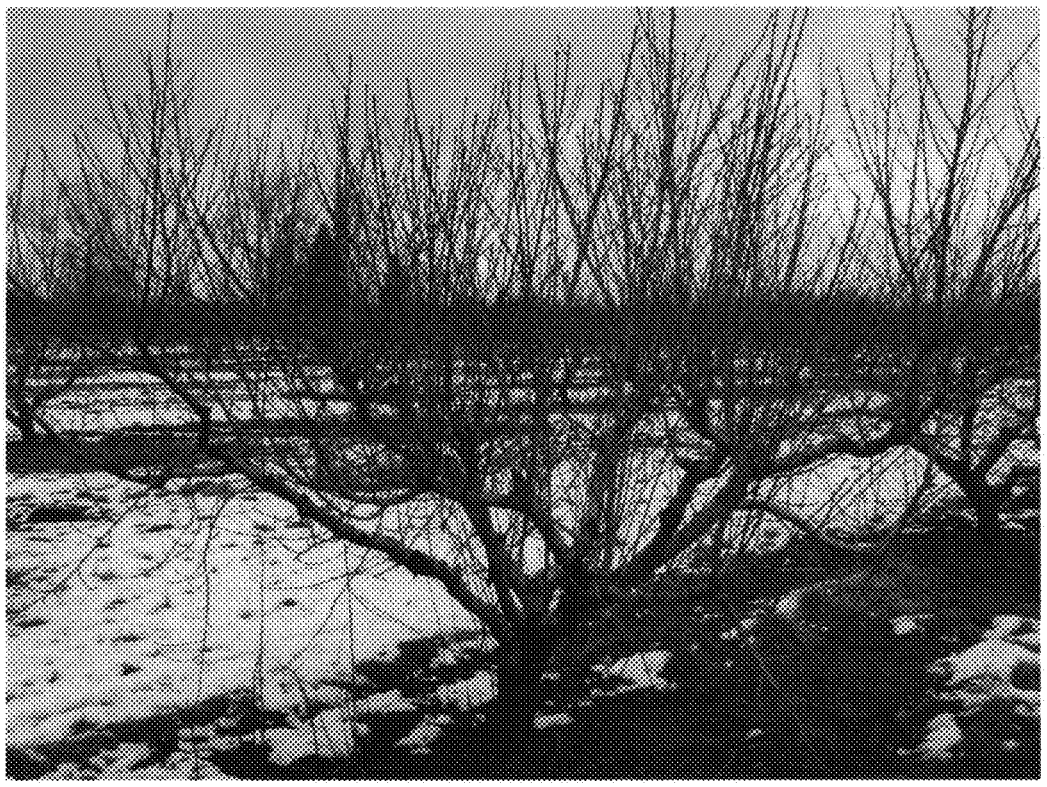
FIG. 4 is a color photograph of a dormant tree of 'NJN102', prior to pruning, in late winter that illustrates the rounded, spreading growth habit of a tree at said fruit research in Cream Ridge, N.J. on Feb. 8, 2016.
Figure 5:
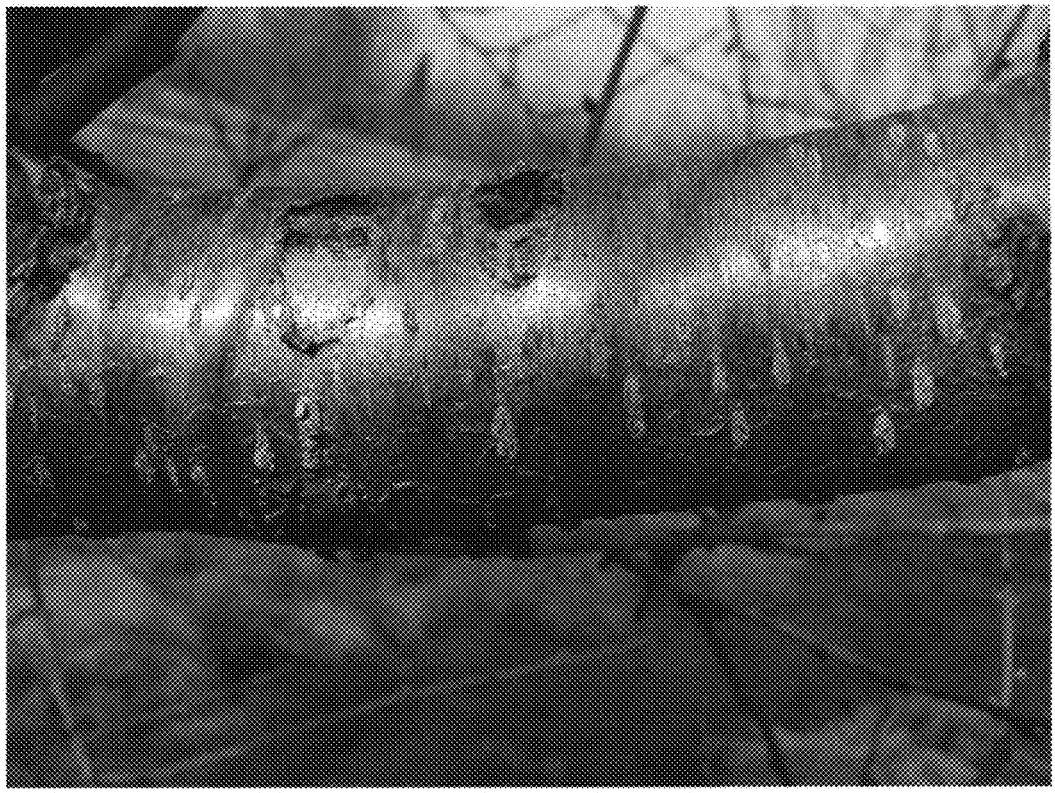
FIG. 5 is a color photograph taken on Mar. 11, 2015 of immature bark of 'NJN102' that illustrates color and the moderate density of conspicuous, elliptic lenticels on the immature bark.
Figure 6:
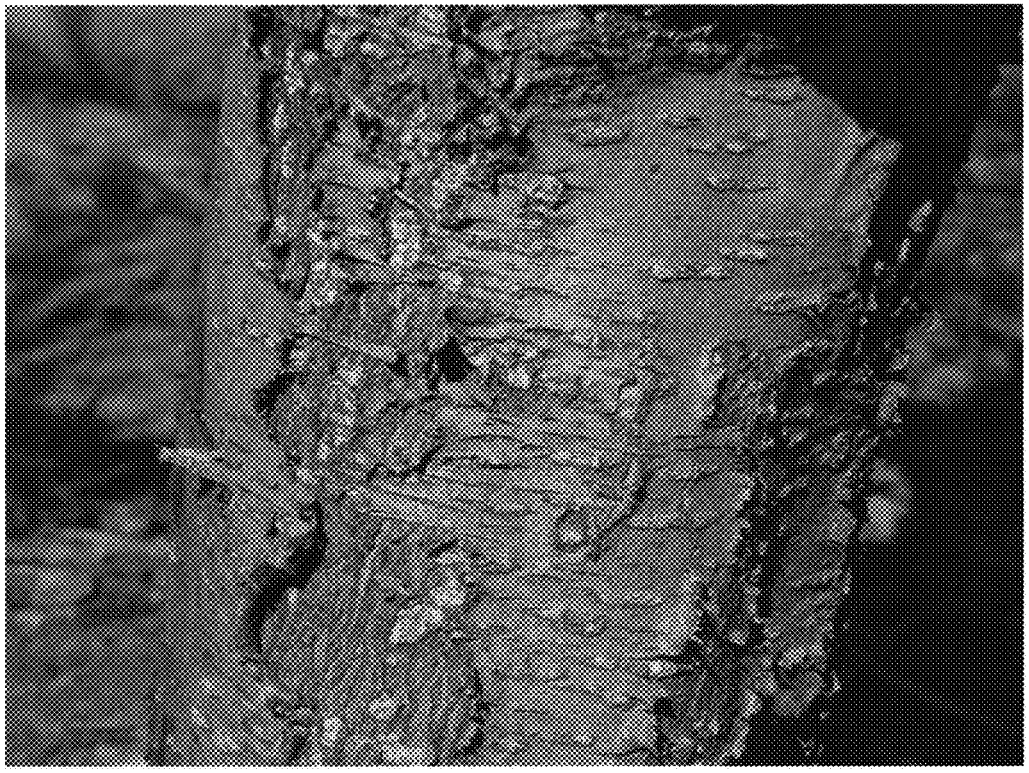
FIG. 6 is a color photograph taken on Mar. 15, 2015 of mature bark of 'NJN102' that illustrates the rough, greyed-green color and shallow furrows of the mature bark.

The colors of and illustration of this type may vary with lighting and other conditions under such conditions and, therefore, color characteristics of this new variety should be determined with reference to the observations described herein, rather than from these illustrations alone.

DETAILED BOTANICAL DESCRIPTION

The following detailed description of the 'NJN102' variety is based on observations of an asexually reproduced tree. The observed tree was six years of age and growing on 'Lovell' seedling rootstock (non-patented) at the fruit research farm in Cream Ridge, N.J.

Scientific name: *Prunus persica* var. *nucipersica*.

Parentage:

*Seed parent*.—'Fantasia'.

*Pollen parent*.—'Eastern Glo'.

Tree:

*Vigor*.—Vigorous.

*Plant hardiness zone*.—Growth of plants has only been observed in zone 6b.

*Dormant flower bud cold tolerance*.—At least to −20° C.

*Leaf bud burst*.—Typically in mid-April when grown in Cream Ridge, N.J., but can vary by one to two weeks.

*Overall shape*.—Rounded, spreading.

*Height*.—Average as compared to other nectarine cultivars. For example, measurement of a typical grafted tree on 'Lovell' peach seedling rootstock (non-patented) at six years after planting shows an average height of 3.3 meters when grown in Cream Ridge, N.J.

*Width*.—Average as compared to other nectarine cultivars. For example, measurement of a typical grafted tree on 'Lovell' peach seedling rootstock (non-patented) at six years after planting shows an average width of 4.3 meters when grown in Cream Ridge, N.J.

*Caliper*.—Six year old tree is 48 cm. in circumference measured at 20 cm. from the ground.

Trunk and branches:

*Trunk bark texture*.—Rough with a few shallow furrows.

*Trunk bark color*.—Greyed-green (between RHS 197C and RHS 197D).

*Primary branches*.—Branches that are approximately 16 cm. in circumference are greyed-orange (RHS 176A) in color, overlaid with grey (RHS 201D). Lenticles: Moderate density, approximately 0.7 per square cm; elliptical in shape and conspicuous; typical examples of which averaged 5.5 mm. in length and 2.6 mm. in width; greyed-green (RHS 198C) in color and may be greyed-orange (RHS 164B) towards the center. Branch pubescence: None. New growth bark: Greyed-purple (RHS 184A) in sun; color yellow-green (RHS 152D) in shade.

*Internodes*.—Length averaging 27.0 mm. on a one-year shoot.

Leaves:

*Texture*.—Glabrous, both surfaces.

*Sheen*.—Young leaves semi-glossy with a flat finish on the underside.

*Length*.—About 169 mm. to 188 mm., averaging about 180 mm. including the petiole.

*Width*.—About 31 mm. to 42 mm., averaging about 40 mm.

*Petiole*.—Averaging 9.8 mm. long and about 2.0 mm. in diameter. Color is yellow-green (145C).

*Margin*.—Crenate.

*Margin undulation*.—Slight to moderate.

*Form*.—Lanceolate, and concave in cross section.

*Apex*.—Sharply acuminate, curved downward.

*Base*.—Cuneate.

*Venation*.—Pinnate.

*Glands*.—Number: About 2 to 3, averaging about 2.2. Position: Generally, located on the leaf margin at its base and petiole. Size: Length averaging 1.7 mm. and width averaging 1.0 mm. Form: Reniform.

*Stipules*.—Stipules are present on immature leaves, but they are not persistent. Typically, there are two per immature leaf, with an average length of 8.0 mm. The color is yellow-green (152 B). None observed on mature leaves.

*Leaf color*.—Upper leaf surface: Yellow-green (between RHS 146A and RHS 147A). Lower leaf surface: Yellow-green (RHS 147B). Vein: Yellow-green (RHS 145C).

*Pubescence*.—None.

Flowers:

*Size*.—Large size, typical flower measuring between 34 mm. to 42 mm., averaging about 38 mm. across.

*Color*.—Dormant bud: Grey (RHS 201C). Pink stage bud: Red-purple (between RHS 62C and RHS 62D). Open flower: Red (between RHS 62C and RHS 62D).

*Petals*.—Typically five petals per flower; cupped, nearly round, averaging about 18.7 mm. long and 17.5 mm. wide.

*Upper petal color*.—Red (between RHS 62C and RHS 62D).

*Lower petal color*.—Red (between RHS 62C and RHS 62D).

*Petal apex*.—Obtuse, nearly rounded.

*Petal base*.—Cuneate.

*Stamens*.—Position: Perigynous and near the point of attachment of the petals. Number: Variable, typical range 34 and 43, averaging 39.3. Length: Variable, between 8 mm. to 13 mm., averaging 10.5 mm. Filament color: White (RHS 157D). Anther color: Greyed-red (RHS 180B).

*Pistil*.—Number: One. Size: Length between 17 and 20 mm., averaging 18.6 mm. Pistil color: Yellow-green (RHS 145C). Ovary: Glabrous and ellipsoid in shape, color yellow-green (RHS 145C).

*Stigma*.—Located at approximately the same level as the longest stamens.

*Sepals*.—Number: Five. Pubescence: Length short to long, with moderate density, increasing toward the edge. Color: Yellow-green (RHS 146C) with a greyed-purple (RHS 183A) over color. Shape: Triangular, with a rounded apex. Size: Length averaging 5.4 mm., width averaging 5.0 mm.

*Nectar cup color*.—Greyed-orange (RHS 168B).

*Pollen*.—Viable and abundant, plant is typically self-fruitful; yellow (RHS 11A) in color.

*Fragrance*.—Very slight.

*Bloom season*.—Onset of bloom in 2014 on April 16; full bloom on April 24.

Fruit:

*Size*.—Medium to large, averaging about 6.6 cm long, 6.5 cm. wide parallel to the suture and 6.4 cm. wide perpendicular to the suture.

*Typical weight*.—152 g.

*Form*.—Longitudinal section: Nearly round. Traverse section: Nearly round.

*Suture*.—Shallow, slightly lipped.

*Ventral surface*.—Typically smooth.

*Base*.—Flat.

*Apex*.—Mostly flat to slightly depressed; apex tip is a point.

*Stem*.—Average length of 7.2 mm. and an average diameter of 3.8 mm.

*Skin*.—Thickness: Medium. Surface: Glabrous, typically glossy. Tenacity: Medium. Astringency: None. Tendency to crack: Low. Color: Greyed-purple (RHS 185A) blush; ground color yellow-orange (RHS 14B).

*Fruit properties*.—Flesh color: Yellow-orange (RHS 18A) becoming red (between RHS 45D and RHS 51C), toward the stone. Flesh adhesion: Freestone when fully mature. Flesh firmness: Average. Juice: Moderate. Texture: Firm, but melting. Fibers: Not noticeable. Ripens: Between July 21 and July 31 at Cream Ridge, N.J. Flavor: Typically sweet and moderately acidic. Soluble solids: 12.2%. Aroma: Medium. Eating quality: Good to very good.

*Keeping quality*.—Medium. Has held its flavor and firmness for at least 14 days in cold storage at 1° C. to 2° C.

*Shipping quality*.—Good. No bruising or scaring disorders have been observed.

*Usage*.—Dessert.

*Market*.—Local and long distance.

*Productivity*.—Excellent. Trees have produced a full crop in 9 out of 10 years at Cream Ridge, N.J. However, productivity varies greatly depending upon conditions inclusive of winter and spring temperatures, rainfall, tree density, pruning methods, soil type, fertilization, irrigation, degree of fruit thinning.

Stone:

*Type*.—Semi-freestone becoming freestone when soft ripe.

*Form*.—Obovate.

*Base*.—Medium.

*Apex*.—Medium.

*Surface*.—Chains of pits and grooves.

*Ventral suture*.—Medium.

*Dorsal ridge*.—Low to medium height, narrow width, forming lines of medium depth.

*External color*.—Greyed-orange (RHS 168D) overlaid with greyed-red (RHS 181B).

*Cavity surface color*.—Greyed orange (RHS 165D).

*Average stone dry weight*.—5.4 g.

*Average stone wall thickness*.—Varies between 3.5 mm. along the dorsal ridge to 9.1 mm. at the base.

*Size*.—Averages about 35.4 mm. long, 28.4 mm. wide parallel to the dorsal ridge, and 17.9 mm. wide perpendicular to the dorsal ridge.

*Tendency to split*.—Low.

Kernel:

*Form*.—Elliptic to slightly obovate.

*Skin color*.—Greyed-orange (RHS 165B).

*Vein color*.—Greyed-orange (between RHS 166B and RHS 166C).

*Viability*.—Yes, but may need to be germinated in tissue culture.

*Size*.—Averages about 17.3 mm. long, 11.0 mm. wide, and 1.7 mm. in breadth.

Plant/fruit disease and pest resistance/susceptibility: No atypical resistances/susceptibilities have been noted under normal cultural practices.

We claim:

1. A new and distinct variety of nectarine tree, substantially as herein shown and described.

* * * * *